US009993543B2

United States Patent
Stedman et al.

(10) Patent No.: US 9,993,543 B2
(45) Date of Patent: Jun. 12, 2018

(54) IMMUNOGENIC COMPOSITIONS COMPRISING SILICIFIED VIRUS AND METHODS OF USE

(71) Applicants: Portland State University, Portland, OR (US); Providence Health & Services—Oregon, Portland, OR (US)

(72) Inventors: Kenneth M. Stedman, Portland, OR (US); James R. Laidler, Portland, OR (US); Keith Bahjat, Portland, OR (US)

(73) Assignees: Portland State University, Portland, OR (US); Providence Health & Services—Oregon, Portland, OR (US)

( * ) Notice: Subject to any disclaimer, the term of this patent is extended or adjusted under 35 U.S.C. 154(b) by 0 days. days.

(21) Appl. No.: 14/763,947

(22) PCT Filed: Jan. 31, 2014

(86) PCT No.: PCT/US2014/014284
§ 371 (c)(1),
(2) Date: Jul. 28, 2015

(87) PCT Pub. No.: WO2014/121132
PCT Pub. Date: Aug. 7, 2014

(65) Prior Publication Data
US 2015/0359871 A1    Dec. 17, 2015

Related U.S. Application Data

(60) Provisional application No. 61/759,131, filed on Jan. 31, 2013.

(51) Int. Cl.
| | |
|---|---|
| *A61K 39/12* | (2006.01) |
| *C12N 7/00* | (2006.01) |
| *A61K 39/125* | (2006.01) |
| *A61K 39/13* | (2006.01) |
| *A61K 39/145* | (2006.01) |
| *A61K 39/15* | (2006.01) |
| *A61K 39/21* | (2006.01) |
| *A61K 39/215* | (2006.01) |
| *A61K 39/235* | (2006.01) |

(Continued)

(52) U.S. Cl.
CPC ............ *A61K 39/12* (2013.01); *A61K 39/125* (2013.01); *A61K 39/13* (2013.01); *A61K 39/145* (2013.01); *A61K 39/15* (2013.01); *A61K 39/21* (2013.01); *A61K 39/215* (2013.01); *A61K 39/235* (2013.01); *A61K 39/285* (2013.01); *A61K 39/29* (2013.01); *A61K 39/292* (2013.01); *C12N 7/00* (2013.01); *A61K 2039/525* (2013.01); *A61K 2039/5252* (2013.01); *A61K 2039/55505* (2013.01); *A61K 2039/55561* (2013.01); *A61K 2039/55566* (2013.01); *A61K 2039/55588* (2013.01); *C12N 2710/10021* (2013.01); *C12N 2710/10034* (2013.01); *C12N 2710/24121* (2013.01); *C12N 2710/24134* (2013.01); *C12N 2720/12321* (2013.01); *C12N 2720/12334* (2013.01); *C12N 2740/16021* (2013.01); *C12N 2740/16034* (2013.01); *C12N 2760/16021* (2013.01); *C12N 2760/16034* (2013.01); *C12N 2770/20021* (2013.01); *C12N 2770/20034* (2013.01); *C12N 2770/24021* (2013.01); *C12N 2770/24034* (2013.01); *C12N 2770/24221* (2013.01); *C12N 2770/24234* (2013.01); *C12N 2770/32421* (2013.01); *C12N 2770/32434* (2013.01); *C12N 2770/32621* (2013.01); *C12N 2770/32634* (2013.01); *C12N 2795/10134* (2013.01); *C12N 2795/14034* (2013.01)

(58) Field of Classification Search
None
See application file for complete search history.

(56) References Cited

U.S. PATENT DOCUMENTS

| | | |
|---|---|---|
| 2003/0104056 A1 | 6/2003 | Rudnic et al. |
| 2011/0014472 A1 | 1/2011 | Culver et al. |

(Continued)

FOREIGN PATENT DOCUMENTS

| | | |
|---|---|---|
| JP | 2002-017370 | 1/2002 |
| RU | 2 440 098 | 1/2009 |

(Continued)

OTHER PUBLICATIONS

Wang et al., "Hydrated Silica Exterior Produced by Biomimetic Silicification Confers Viral Vaccine Heat-Resistance," *ACS Nano* 9(1):799-808, 2015.

(Continued)

*Primary Examiner* — Stacy B Chen
(74) *Attorney, Agent, or Firm* — Klarquist Sparkman, LLP

(57) ABSTRACT

It is disclosed herein that viruses coated in silica retain infectivity and the capacity to induce an immune response in an infected host. In addition, silicified virus is remarkably resistant to desiccation. Provided herein are methods of inducing a virus-specific immune response in a subject by administering to the subject an effective amount of silicified virus or silicified virus particles. Methods of enhancing a virus-specific cell-mediated immune response (such as a T cell-mediated immune response) in a subject by administering to the subject a silicified virus or silicified virus particles are also described herein. Further provided are immunogenic compositions comprising silicified virus or silicified virus particles, such as compositions useful as vaccines. The immunogenic compositions include a pharmaceutically acceptable carrier and/or an adjuvant.

20 Claims, 7 Drawing Sheets

(51) Int. Cl.
    *A61K 39/285*     (2006.01)
    *A61K 39/29*     (2006.01)
    *A61K 39/00*     (2006.01)

(56) References Cited

U.S. PATENT DOCUMENTS

| | | |
|---|---|---|
| 2011/0104293 A1 | 5/2011 | Pulendran et al. |
| 2011/0123620 A1 | 5/2011 | Weigandt et al. |
| 2011/0275139 A1 | 11/2011 | Kohara et al. |
| 2013/0288338 A1 | 10/2013 | Kohara et al. |

FOREIGN PATENT DOCUMENTS

| | | |
|---|---|---|
| WO | WO 2009/110644 | 9/2009 |
| WO | WO 2011/098837 | 8/2011 |
| WO | WO 2012/050229 | 4/2012 |
| WO | WO 2012/162428 | 11/2012 |

OTHER PUBLICATIONS

Alcock et al., "Long-Term Thermo stabilization of Live Poxviral and Adenoviral Vaccine Vectors at Supraphysiological Temperatures in Carbohydrate Glass," Vaccines, vol. 2, 8 pages, 2010.

Kyle et al., "Preservation Potential of Lipid-Containing Viruses under Silicifying Conditions," *43$^{rd}$ Lunar and Planetary Science Conference*, 2012.

Laidler et al., "Differential Activation, Reactivation and Des sication Tolerance of Silicified Viruses," abstract presented at the Astrobiology Science Conference, Apr. 17, 2012, Atlanta, Georgia.

Laidler et al., "Virus Silicification under Simulated Hot Spring Conditions," *Astrobiology*, vol. 10:569-576, 2010.

Laidler et al., "Reversible Inactivation and Desiccation Tolerance of Silicified Viruses," *J. Virol.*, vol. 87:13927-13929, 2013.

Orange et al., "Experimental fossilisation of Viruses from extremophilic Archaea," *Biogeosciences*, vol. 8:1465-1475, 2011.

Royston et al., "Characterization of Silica-Coated Tobacco Mosaic Virus," *J. Colloid Interface Sci.*, vol. 298:706-712, 2006.

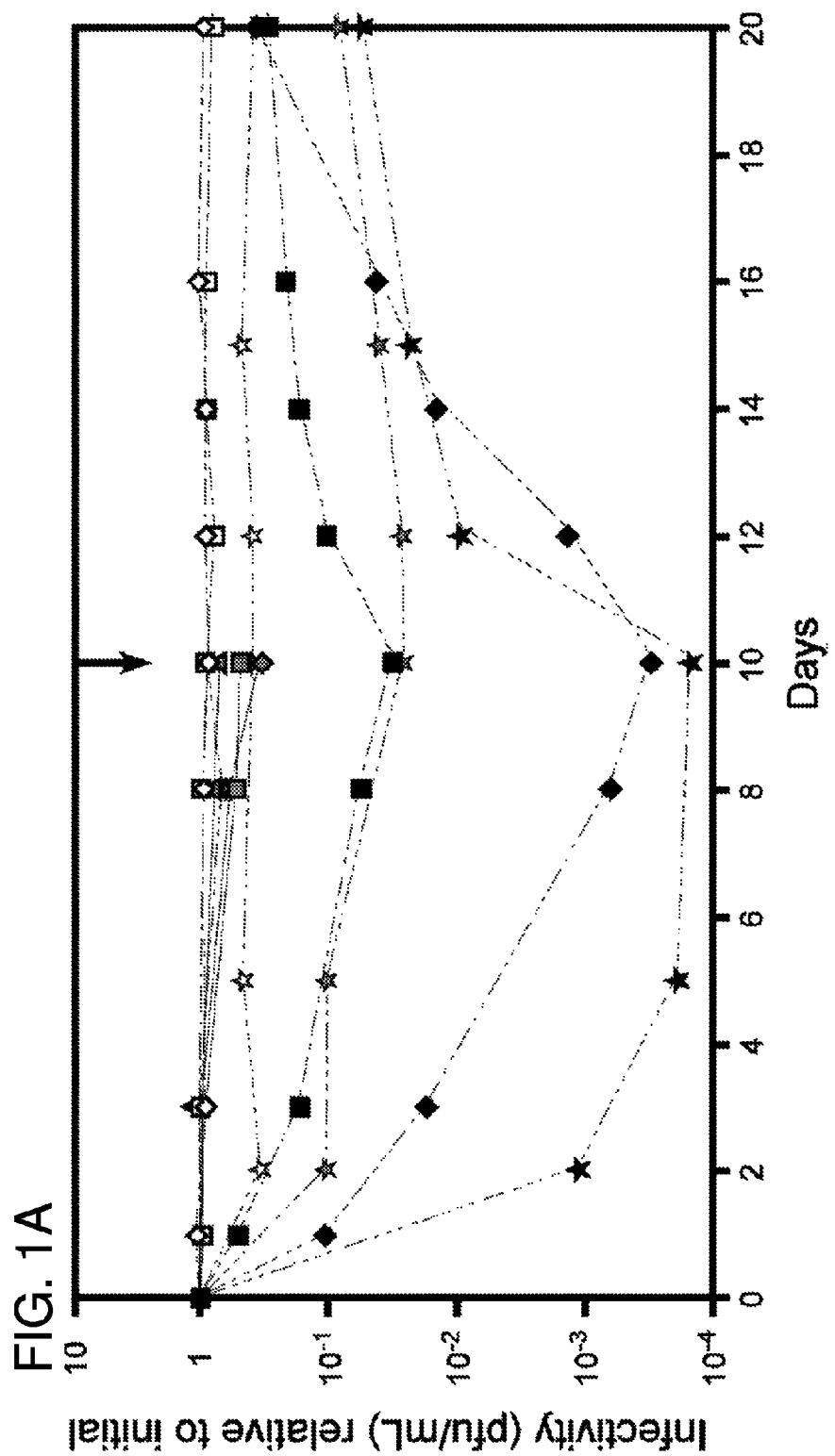

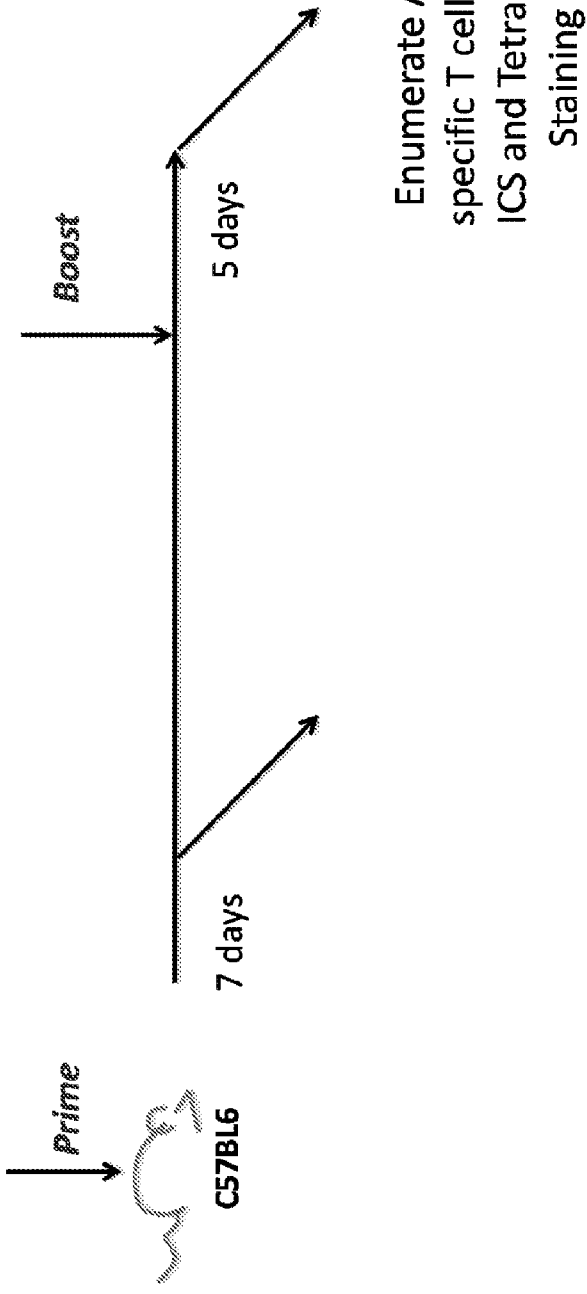

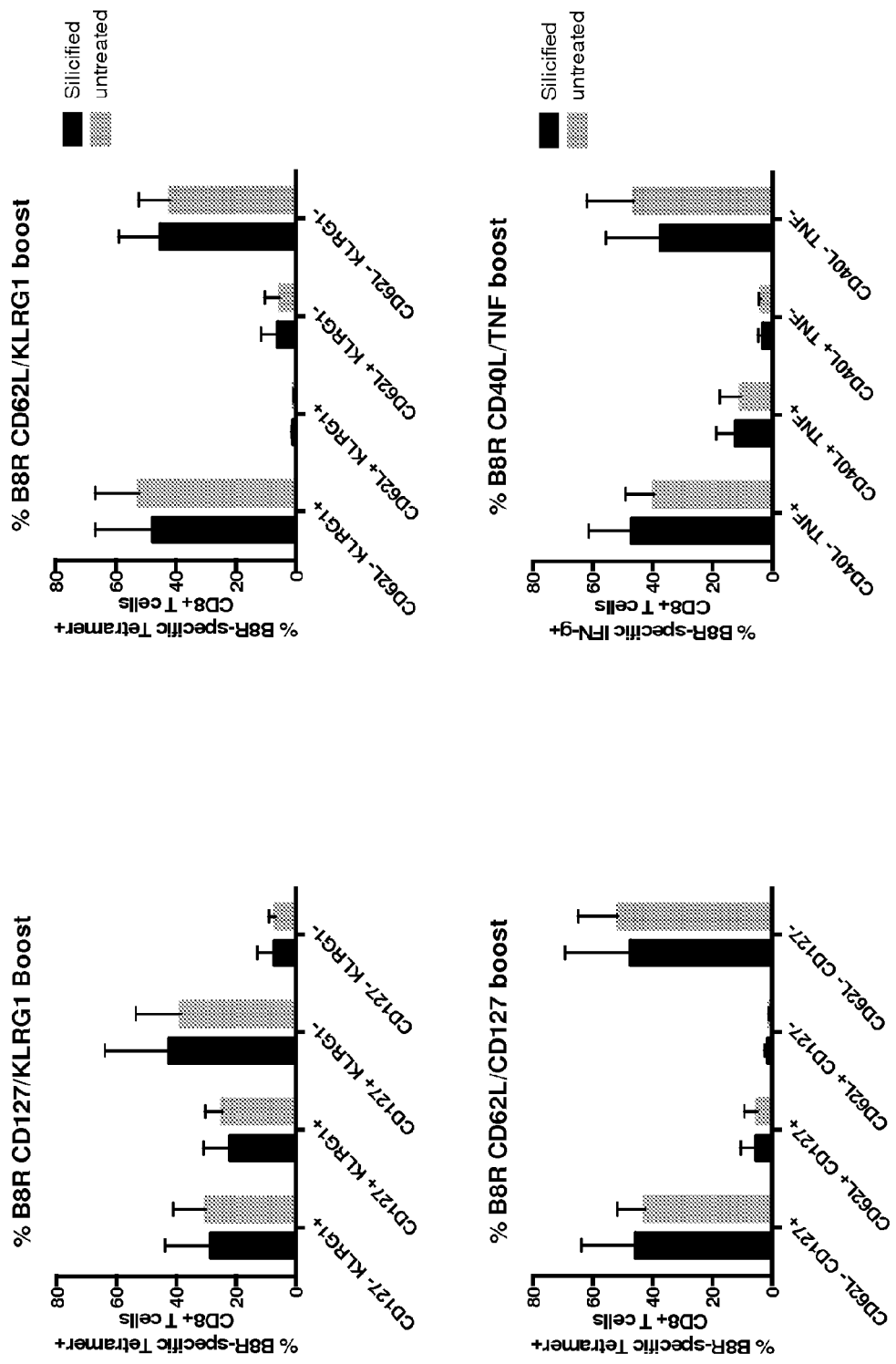

IMMUNOGENIC COMPOSITIONS COMPRISING SILICIFIED VIRUS AND METHODS OF USE

CROSS REFERENCE TO RELATED APPLICATIONS

This application is the U.S. National Stage of International Application No. PCT/US2014/014284, filed Jan. 31, 2014, published in English under PCT Article 21(2), which claims the benefit of U.S. Provisional Application No. 61/759,131, filed Jan. 31, 2013, which is herein incorporated by reference in its entirety.

ACKNOWLEDGMENT OF GOVERNMENT SUPPORT

This invention was made with government support under grant number NNA11AC01G awarded by the National Aeronautics and Space Administration, and grant number DGE:0114427 awarded by the National Science Foundation. The government has certain rights in the invention.

FIELD

This disclosure concerns the preservation of viruses and related particles by coating them in silica. This disclosure further concerns immunogenic compositions comprising silicified virus or virus particles and their use for inducing or altering an immune response in a subject.

BACKGROUND

The mechanism of virus dispersal, especially viruses of organisms endemic to isolated "island" ecosystems (e.g. hot springs), are poorly understood and hotly debated. There is disagreement over whether virus species are cosmopolitan (Breitbart and Rohwer, *Trends Microbiol* 13:278, 2005) or show regional endemism. While some studies show sharp regional differences between virus genomes (Whitaker et al., *Science* 301:976, 2003), suggesting limited dispersal, several others have discovered global distribution of certain viruses with nearly identical genomes (Breitbart et al., *FEMS Microbiol Lett* 236:249, 2004; Short and Suttle, *Appl Environ Microbiol* 71:480, 2005). Given the importance of viruses in maintaining microbial diversity and recycling nutrients (Suttle, *Nat Rev Microbiol* 5:801, 2007), anything that affects virus dispersal will have a significant ecological impact.

One study has shown that local virus dispersal can result from aerosolization of the virus by hot spring fumaroles (Snyder et al., *Proc Natl Acad Sci USA* 104:19102, 2007), suggesting that more distant spread is possible if the particles can reach the upper level winds (Smith et al., *Aerobiologia* 26:35, 2010). A limiting factor of wind-borne virus spread is the ability of the virus to resist drying; most viruses are very sensitive to desiccation (Ding et al., *Gynecol Oncol* 121:148, 2011; Fogarty et al., *Virus Res* 132:140, 2008; Nakano et al., *Fish Pathol* 33:65, 1998) and will rapidly lose infectivity in aerosol form.

Previous studies have shown that viruses can be coated with silica under simulated hot spring conditions (Laidler and Stedman, *Astrobiology* 10:569, 2010; Orange et al., *Biogeosciences* 8:1465, 2011). However, prior to the present disclosure, it was unknown whether viruses coated in silica retain infectivity or the capacity to induce an immune response in an infected host.

SUMMARY

It is disclosed herein that silicified virus particles retain the capacity to infect host cells and induce a virus-specific immune response in vivo.

Provided is a method of inducing a specific immune response (e.g., a virus-specific immune response) to selected antigen(s) (e.g., viral antigens) in a subject by administering to the subject an effective amount of silicified virus/virus particles. In some embodiments, the immune response includes activation of virus-specific T cells, production of virus-specific antibodies, cytokine production, or any combination thereof.

Also provided are immunogenic compositions comprising a silicified particle (e.g., a silicified viral particle) and a pharmaceutically acceptable carrier and/or an adjuvant.

Further provided is a method of enhancing an antigen- (e.g., virus antigen-) specific cell-mediated immune response in a subject by administering to the subject a silicified virus or silicified virus particles, wherein the antigen-specific cell-mediated immune response is increased relative to the cell-mediated immune response following administration of non-silicified virus or virus particles. In some embodiments, an increase in the virus-specific cell-mediated immune response is determined by an increase in the number of virus-specific T cells, an increase in activation of virus-specific T cells, an increase in cytokine production, or any combination thereof.

In some embodiments of the disclosed methods and compositions, the virus infects eukaryotic cells, such as animal cells. In particular examples, the virus is a mammalian virus.

The foregoing and other objects, features, and advantages of the invention will become more apparent from the following detailed description, which proceeds with reference to the accompanying figures.

BRIEF DESCRIPTION OF THE DRAWINGS

FIG. 1A is a graph showing reversible inactivation of viruses by silica treatment. Shown is the effect of silicification on infectivity of bacteriophage T4 (diamonds), SSV-K (squares), PRD1 (triangles) and VACV (stars), normalized to initial infectivity. Black symbols are 600 ppm (10 mM) silica solution, grey symbols are 300 ppm (5 mM) and white symbols are control (0 ppm silica). Vertical black arrow indicates transfer to low silica. All plaque assays were performed in triplicate on triplicate biological replicates except for VACV, which had only a single biological replicate. Error bars are obscured by data point symbols.

FIG. 2 is a schematic of the experimental design to evaluate immune responses in mice following administration of silicified and non-silicified VACV.

FIG. 6 is a series of graphs showing the percentage of VACV B8R antigen-specific effector and memory T cells following booster administration of silicified and non-silicified VACV.

DETAILED DESCRIPTION

Figure 1B:
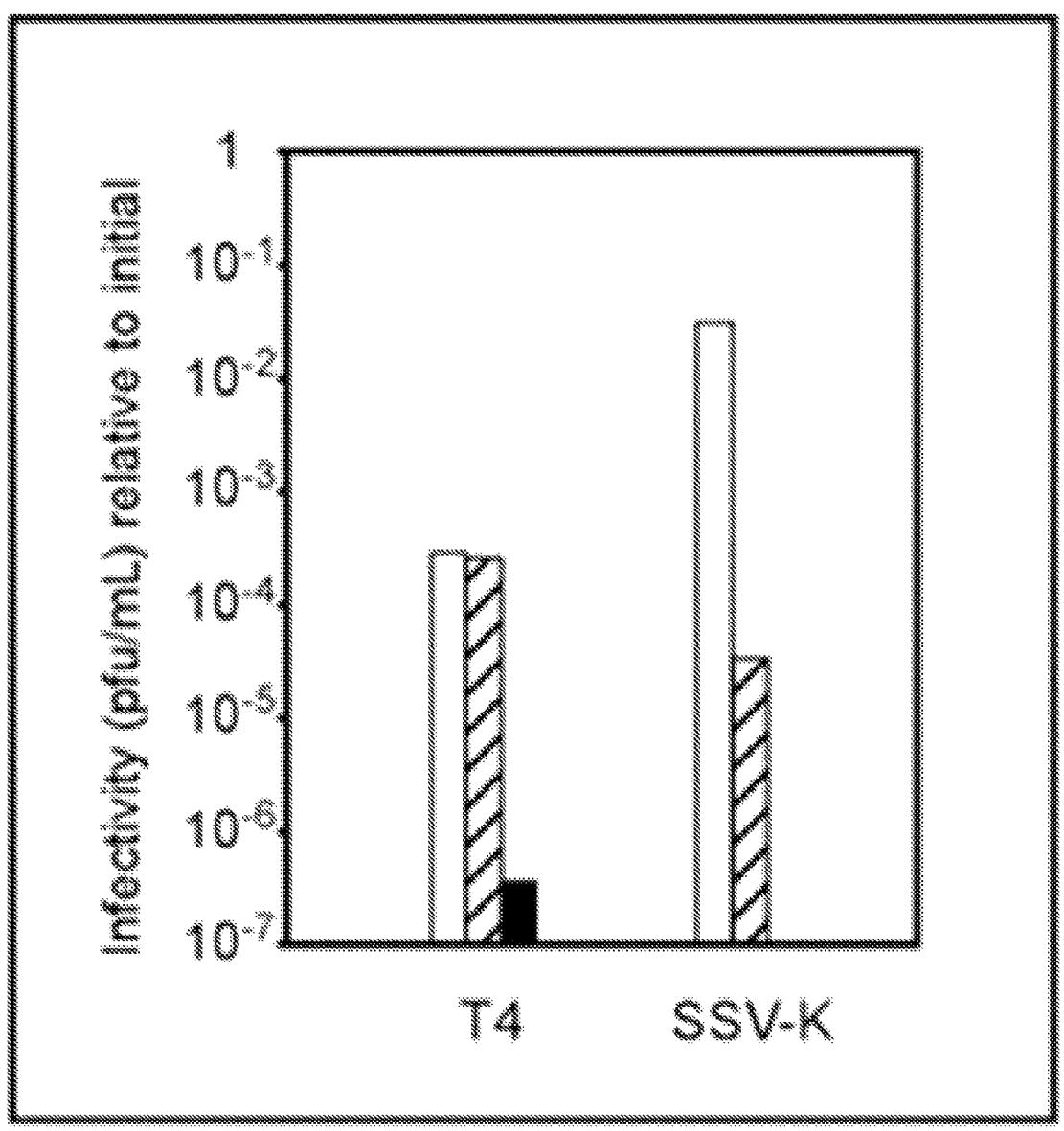
FIG. 1B is a graph showing that silicified viruses are resistant to desiccation. Shown is the effect of silicification on infectivity of silicified viruses (T4 and SSV-K) after desiccation, normalized to the initial infectivity. White bars are infectivity after ten days of silicification; cross-hatched bars are after ten days of desiccation and ten days of rehydration; black bars are after thirty days of desiccation and ten days of rehydration.

I. Abbreviations

ELISA enzyme-linked immunosorbent assay
HIV human immunodeficiency virus
IFN interferon
IL interleukin
MHC major histocompatibility complex
MWCO molecular weight cut-off
PFU plaque forming unit
SSV-K *Sulfolobus* spindle-shaped virus-Kamchatka 1
TGF transforming growth factor
TNF tumor necrosis factor
VACV vaccinia virus II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); Robert A. Meyers (ed.), *Molecular Biology and Biotechnology: a Comprehensive Desk Reference*, published by VCH Publishers, Inc., 1995 (ISBN 1-56081-569-8); and "Virus Taxonomy: Eighth Report of the International Committee on Taxonomy of Viruses," published by Elsevier Academic Press, 2005 (ISBN 0-12-249951-4, Claude M. Fauquet et al., Eds).

In order to facilitate review of the various embodiments of the disclosure, the following explanations of specific terms are provided:

Adenovirus: A non-enveloped virus with icosahedral geometry and having a double-stranded, linear DNA genome. There are approximately 57 known serotypes of adenoviruses that infect humans, which are responsible for 5-10% of upper respiratory infections in children.

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules and pattern recognition receptor agonists (such as toll-like receptor agonists). Toll-like receptor (TLR) agonists include, for example, TLR3 agonists (e.g., synthetic dsRNA such as poly I:C), TLR4 agonists (e.g., monophosphoryl lipid A), TLR7/8 agonists (e.g., imidazoquinoline compounds such as imiquimod and resiquimod, single-stranded polyU), TLR9 agonists (e.g., CpG oligodeoxynucleotides). Other exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition (e.g. an immunogenic composition) to a subject means to give, apply or bring the composition into contact with the subject. Administration can be accomplished by any of a number of routes, such as, for example, topical, oral, subcutaneous, inhalation, intraperitoneal, intravenous, intrathecal and intramuscular.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In the context of the present disclosure, the term "antigen" includes, for example, native antigens (such as antigens present on a wild-type virus particle) or antigens of a recombinant or engineered virus particle.

Cell-mediated immunity: An immune response that does not involve antibodies, but rather involves the activation of phagocytes, natural killer (NK) cells, antigen-specific cytotoxic T-lymphocytes, and the release of various cytokines in response to an antigen. Historically, the immune system was separated into two branches—humoral immunity, for which the protective function of immunization could be found in the humor (cell-free bodily fluid or serum) and cellular immunity, for which the protective function of immunization was associated with cells. $CD4^+$ T cells or helper T cells provide protection against different pathogens. Cytotoxic T cells cause death by apoptosis without using cytokines, therefore in cell mediated immunity cytokines are not always present. Cellular immunity protects the body by activating antigen-specific cytotoxic T-lymphocytes that are able to induce apoptosis in body cells displaying epitopes of foreign antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses. Cell-mediated immunity is directed primarily at microbes that survive in phagocytes and microbes that infect non-phagocytic cells. It is most effective in removing virus-infected cells, but also participates in defending against fungi, protozoans, cancers, and intracellular bacteria. As used herein, a "T cell-mediated immune response" is an immune response characterized by the production and/or activation of antigen-specific (such as virus-specific) T cells. A T cell-mediated immune response can include a cytotoxic T cell response and/or a T helper cell response.

Cytokines: Protein molecules that are secreted by cells and function as signaling molecules. Cytokines generally refer to immunomodulatory proteins including, for example, interleukins (e.g., IL-1 to IL-20), interferons (e.g., IFN-α, IFN-β, IFN-γ), transforming growth factor (TGF) proteins (e.g., TGF-β1, TGF-β2 and TGF-β3) tumor necrosis factor (TNF) family members (e.g., TNF-α, TNF-β, LT-β, CD154, TRAIL), as well as other molecules involved in immune regulation (e.g., erythropoietin, stem cell factor, M-CSF).

Flavivirus: Flaviviruses are members of the family Flaviviridae, and include the well-characterized viruses West Nile virus, dengue virus (dengue virus types 1-4), tick-borne encephalitis virus, yellow fever virus, Japanese encephalitis virus, Powassan virus and St. Louis encephalitis virus. Flaviviruses are enveloped viruses with icosahedral symmetry and a positive-sense single-stranded RNA genome.

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). As used herein, a therapeutic immune response refers to an immune response that treats a viral infection, such as by aiding in viral clearance. Methods of measuring immune responses are well known in the art and include, for example, measuring proliferation and/or activity of lymphocytes (such as B or T cells), secretion of cytokines or chemokines, inflammation, antibody production and the like.

Immunize: To render a subject protected from a disease (for example, an infectious disease), such as by vaccination.

Immunogenic composition: A term used herein to mean a composition useful for stimulating or eliciting a specific immune response (or immunogenic response) in a subject. The immunogenic composition includes a silicified virus. In some embodiments, the immunogenic response is protective or provides protective immunity, in that it enables the subject to better resist infection with or disease progression from the virus against which the immunogenic composition is directed.

Without wishing to be bound by a specific theory, it is believed that an immunogenic response induced by an immunogenic composition may arise from the generation of an antibody specific to one or more of the epitopes provided in the immunogenic composition. Alternatively, the response may comprise a T-helper or cytotoxic T cell-based response to one or more of the epitopes provided in the immunogenic composition. All three of these responses may originate from naïve or memory cells. One specific example of a type of immunogenic composition is a vaccine.

In some embodiments, an "effective amount" or "immune-stimulatory amount" of an immunogenic composition is an amount which, when administered to a subject, is sufficient to engender a detectable immune response. Such a response may comprise, for instance, generation of an antibody specific to one or more of the epitopes provided in the immunogenic composition. Alternatively, the response may comprise a T-helper or CTL-based response to one or more of the epitopes provided in the immunogenic composition. All three of these responses may originate from naïve or memory cells. In other embodiments, a "protective effective amount" of an immunogenic composition is an amount which, when administered to a subject, is sufficient to confer protective immunity upon the subject. In other embodiments, a "therapeutic effect amount" of an immunogenic composition is an amount which, when administered to a subject, is sufficient to treat a viral infection, such as increase viral clearance.

Influenza virus: A segmented negative-strand RNA virus that belongs to the Orthomyxoviridae family. There are three prevalent types of Influenza viruses, A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H5N1, cause systemic infections in poultry in which mortality may reach 100%. H5N1 is also referred to as "avian influenza." In 2009, H1N1 influenza was the most common cause of human influenza. A new strain of recombinant swine-origin H1N1 emerged in 2009 and was declared pandemic by the World Health Organization. This strain was referred to as "swine flu." H3N2, H2N2 and influenza B viruses also infect humans and are also causative agents of seasonal influenza.

Isolated: An "isolated" or "purified" biological component (such as a nucleic acid, peptide, protein, protein complex, virus or particle) has been substantially separated, produced apart from, or purified away from other biological components, such as other chromosomal and extra-chromosomal DNA and RNA, and proteins. Nucleic acids, peptides, proteins and viruses that have been "isolated" or "purified" thus include nucleic acids, proteins and viruses purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment (such as within a cell, or other production vessel). Preferably, a preparation is purified such that the biological component represents at least 50%, such as at least 70%, at least 90%, at least 95%, or greater, of the total biological component content of the preparation.

Lentivirus: A genus of viruses in the Retroviridae family, characterized by a long incubation period. Lentiviruses are capable of infecting non-dividing cells, which distinguishes these viruses from other types of retroviruses. Lentiviruses are enveloped viruses having a genome that consists of two identical single-stranded RNA segments, which are reverse transcribed into DNA upon infection of host cells. Lentiviruses include, for example, human immunodeficiency virus (HIV; including HIV-1 and HIV-2), simian immunodeficiency virus (SW) and feline immunodeficiency virus (FIV). Lentiviruses are commonly used as the basis for gene therapy vectors.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of immunogenic compositions.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Parvovirus: Any virus belonging to the family Parvoviridae. Parvoviruses are small (about 18-26 nanometers in diameter), non-enveloped viruses with a single-stranded DNA genome and an icosahedral capsid. Parvoviruses include, for example, murine minute virus, canine parvovirus, the human parvovirus B19, and adeno-associated viruses (AAV). Parvoviruses are also commonly used as gene therapy agents.

PhiX174: A well-studied bacteriophage in the family Microviridae with a circular, single-stranded DNA genome encoding 11 proteins. PhiX174 is a small (about 30 nm in diameter), non-enveloped virus.

Picornavirus: Any virus belonging to the family Picornaviridae. Picornaviruses are non-enveloped, positive-stranded RNA viruses with a small (about 30 nm in diameter) icosahedral capsid. Picornaviruses are separated into a number of genera and include many important pathogens of humans and animals. The diseases they cause are varied, ranging from acute common cold-like illnesses, to poliomyelitis, to chronic infections in livestock. Picornaviruses include, for example, enteroviruses (such as poliovirus and coxsackie virus), rhinoviruses, foot-and-mouth disease virus, encephalomyocarditis viruses, and hepatitis A virus.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of one or more signs or symptoms of a disease.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Rotavirus: A non-enveloped, double-stranded RNA virus with icosahedral symmetry. Rotavirus is the most common cause of severe diarrhea among infants and young children. There are seven species of rotavirus, referred to as A, B, C, D, E, F and G.

Silica: The dioxide of silicon ($SiO_2$) occurring in crystalline, amorphous and impure forms (as in quartz, opal and sand, respectively). Silica is a refractory insoluble material used in the manufacture of glass, ceramics, and abrasives.

Silicification: The process of coating or impregnating in silica.

Silicified virus or virus particle: A virus or virus particle that has been coated in silica. In some embodiments, a virus or virus particle is considered silicified following incubation in a solution of silica at a concentration of about 100 ppm to about 1000 ppm silica, such as about 150 ppm, about 300 ppm, about 450 ppm, about 600 ppm, about 750 ppm or about 900 ppm silica, for about 1 to about 10 days, such as 1, 2, 3, 4, 5, 6, 7, 8, 9 or 10 days. In some examples, the virus or virus particle is considered silicified following incubation in a solution of silica that is about 300 ppm to about 600 ppm (about 5 mM to about 10 mM) silica for 1 to 10 days. In other embodiments, the virus is silicified following incubation in a solution of silica that is about 100 ppm to about 1000 ppm for at least 10 days, such as (but not limited to) 10 days, 12 days, 14 days, 16 days, 18 days or 20 days. In some embodiments, a virus or virus particle is silicified if at least 75%, at least 80%, at least 85%, at least 90%, at least 95% or 100% of the surface area of the virus or viral particle is coated in silica.

Subject: Living multi-cellular vertebrate organisms, a category that includes both human and non-human mammals.

Therapeutically effective amount: A quantity of a specified agent (such as an immunogenic composition) sufficient to achieve a desired effect in a subject being treated with that agent. For example, this may be the amount of a virus vaccine (such as a silicified virus vaccine) useful for eliciting an immune response in a subject and/or for preventing infection by the virus. In the context of the present disclosure, a therapeutically effective amount of a virus vaccine, for example, is an amount sufficient to increase resistance to, prevent, ameliorate, and/or treat infection caused by a virus in a subject without causing a substantial cytotoxic effect in the subject. The effective amount of a virus immune stimulating composition useful for increasing resistance to, preventing, ameliorating, and/or treating infection in a subject will be dependent on, for example, the subject being treated, the manner of administration of the therapeutic composition and other factors.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins (including virus-like particles), peptides or DNA derived from them. An attenuated vaccine is a virulent organism that has been modified to produce a less virulent form, but nevertheless retains the ability to elicit antibodies and cell-mediated immunity against the virulent form. A killed vaccine is a previously virulent microorganism that has been irreversibly inactivated with chemicals or heat, but elicits antibodies against the virulent microorganism. Vaccines may elicit both prophylactic (preventative) and therapeutic responses. Methods of administration vary according to the vaccine, but may include inoculation, ingestion, inhalation or other forms of administration. Vaccines may be administered with an adjuvant to boost the immune response.

Vaccinia virus (VACV): A large, complex enveloped virus belonging to the poxvirus family. VACV has a linear, double-stranded DNA genome about 190 Kb in length, which encodes approximately 250 genes. Vaccinia virus is well-known for its role as a vaccine that eradicated smallpox.

Virus Particle: The protein capsid component of a wild-type, engineered or recombinant virus. Virus particles include at least one viral structural protein, but may contain multiple structural proteins, depending on the virus. In some instances, the virus particle further includes a lipid envelope. Virus particles may or may not contain nucleic acid (i.e. the viral genome). Thus, in the context of the present disclosure, the term "virus particle" encompasses virus-like particles (VLPs).

Virus: A microorganism that cannot replicate outside of a living cell. Viruses have a nucleoprotein structure consisting of DNA or RNA (or both DNA and RNA), surrounded by a protein capsid or nucleocapsid. Some viruses further possess a lipid envelope. In the context of the present disclosure, a "virus" includes any family, genus, species, strain or subtype of virus. The term "virus" also includes wild-type, recombinant, chimeric and engineered viruses. In some embodiments, the virus infects eukaryotic cells, such as animal cells. In particular embodiments, the virus is a mammalian virus (infects mammalian cells). In some embodiments, the virus is a pathogenic virus (i.e. causes disease to the host). In some embodiments, the virus is an enveloped virus. In other embodiments, the virus is a non-enveloped virus.

Examples of viruses include, but are not limited to those in the following virus families: Retroviridae (for example, human immunodeficiency virus 1 (HIV-1), HIV-2, human T-cell leukemia viruses; Picornaviridae (for example, poliovirus, hepatitis A virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses, including chikungunya virus, equine encephalitis viruses, Simliki Forest virus, Sindbis virus, Ross River virus, rubella viruses); Flaviridae (for example, hepatitis C virus, dengue virus, yellow fever virus, West Nile virus, St. Louis encephalitis virus, Japanese encephalitis virus, Powassan virus and other encephalitis viruses); Coronaviridae (for example, coronaviruses, severe acute respiratory syndrome (SARS) virus and Middle East respiratory syndrome (MERS) coronavirus); Rhabdoviridae (for example, vesicular stomatitis virus, rabies virus); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses, e.g., murine minute virus, canine parvovirus, the human parvovirus B19, and AAV; Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxviridae (variola viruses, vaccinia viruses, pox viruses); and Iridoviridae (such as African swine fever virus); Astroviridae; and unclassified viruses (for example, the agent of delta hepatitis, thought to be a defective satellite of hepatitis B virus).

Virus-like particle (VLP): Virus particles made up of one of more viral structural proteins, but lacking the viral genome.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Virus dispersal is critical for both the spread of disease and the diverse roles that viruses play in the ecology of the Earth (Peterson, *Naturwissenschaften* 95:483, 2008). However, the mechanisms of host-independent virus dispersal, especially of viruses in isolated ecosystems, are poorly understood and hotly debated (Breitbart et al., *FEMS Microbiol Lett* 236:249, 2004; Short and Suttle, *Appl Environ Microbiol* 71:480, 2005). Given the importance of viruses in animal and plant disease and in maintaining microbial diversity and recycling of nutrients on a global scale (Suttle, *Nat Rev Microbiol* 5:801, 2007), anything that affects virus dispersal will have a highly significant ecological impact.

It is disclosed herein that under very mild conditions, diverse viruses can be coated in silica. This silica coating inactivates the virus. However, unlike most virus inactivation regimens, inactivation by silica coating is almost completely reversible (including in vivo). Moreover, it is demonstrated herein that this silica coating provides viruses with remarkable desiccation tolerance. Silicification of viruses thus provides a mechanism for virus preservation, such as for use in vaccine preparation and formulation.

IV. Overview of Several Embodiments

Previous studies have shown that viruses can be coated with silica under simulated hot spring conditions (Laidler and Stedman, *Astrobiology* 10:569, 2010; Orange et al., *Biogeosciences* 8:1465, 2011). However, prior to the present disclosure, it was unknown whether viruses or virus particles coated in silica retain infectivity and the capacity to induce an immune response in an infected host. Disclosed herein is the finding that viruses can be reversibly inactivated by silicification, and the finding that viruses previously subjected to silicification retain the capacity to infect and induce an immune response in a host. It is also disclosed herein that silicified viruses exhibit remarkable resistance to desiccation.

Provided herein is a method of inducing a virus-specific immune response in a subject. In some embodiments, the method includes administering to the subject an effective amount of silicified virus or silicified virus particles. For example, the effective amount can be the amount required to induce a detectable immune response in the host to the virus.

In some embodiments, the virus (or particle thereof) that is silicified is a virus that infects eukaryotic cells, for example animal cells. In particular embodiments, the virus is a mammalian virus. In some embodiments, the virus is vaccinia virus, a rotavirus, an adenovirus, an influenza virus, a lentivirus, a flavivirus, a hepatitis virus, a parvovirus or a picornavirus. In some examples, the lentivirus is an immunodeficiency virus, such as a human immunodeficiency virus, a simian immunodeficiency virus or a feline immunodeficiency virus. In some examples, the flavivirus is West Nile virus, Japanese encephalitis virus, dengue virus, tick-borne encephalitis virus, yellow fever virus, or St. Louis encephalitis virus. In some examples, the hepatitis virus is hepatitis A virus, hepatitis B virus or hepatitis C virus. In some examples, the picornavirus is poliovirus, hepatitis A virus, rhinovirus or foot and mouth disease virus. In some examples, the virus is a parvovirus, such as an adeno-associated virus (AAV), murine minute virus or a canine parvovirus. In other examples, the virus is respiratory syncytial virus.

The virus-specific immune response can be a humoral immune response or a cell-mediated immune response. In some embodiments, the virus-specific immune response comprises activation of virus-specific T cells (such as CD4+ T helper cells or CD8+ cytotoxic T cells), production of virus-specific antibodies, cytokine production, or any combination thereof. Methods of measuring a virus-specific immune response in a host are well known in the art. For example, the number of virus-specific T cells can be evaluated by flow cytometry using antibodies specific for T cell markers (e.g. CD8) and antigen-specific major histocompatibility complex (MHC) tetramers. Virus-specific antibodies can be detected, for example, using an immunoassay, such as an enzyme-linked immunosorbent assay (ELISA). Cytokine production also can be measured by ELISA or flow cytometry using cytokine-specific antibodies.

The route of administration of the silicified virus or silicified virus particles can be any route suitable for inducing an immune response against the particular virus. Suitable immunization routes are well known in the art. In some embodiments, administration is topical, oral, subcutaneous, inhalation, intraperitoneal, intravenous, intrathecal or intramuscular. In particular examples, administration is intramuscular, subcutaneous, oral or inhalation.

Also provided herein are immunogenic compositions comprising a silicified virus or silicified virus particles. In some embodiments, the virus infects eukaryotic cells, for example animal cells. In particular embodiments, the virus is a mammalian virus. In some embodiments, the virus is vaccinia virus, a rotavirus, an adenovirus, an influenza virus, a lentivirus, a flavivirus, a hepatitis virus, or a picornavirus. In some examples, the lentivirus is an immunodeficiency virus, such as a human immunodeficiency virus, a simian immunodeficiency virus or a feline immunodeficiency virus. In some examples, the flavivirus is West Nile virus, Japanese encephalitis virus, dengue virus, tick-borne encephalitis virus, yellow fever virus, or St. Louis encephalitis virus. In some examples, the hepatitis virus is hepatitis A virus, hepatitis B virus or hepatitis C virus. In some examples, the picornavirus is poliovirus.

In some embodiments, the immunogenic composition comprises a pharmaceutically acceptable carrier and/or an adjuvant. In some examples, the adjuvant comprises a water-in-oil emulsion, incomplete Freund's adjuvant, alum, aluminum hydroxide, a toll-like receptor agonist, an immunostimulatory oligonucleotide or a biological adjuvant. In some examples, the pharmaceutically acceptable carrier comprises physiological saline, balanced salt solution, buffering agent, suspending agent, thickening agent, non-aqueous solvent, aqueous carrier, preservative, anti-oxidant, bacateriostat, or any combination thereof.

In some embodiments, the immunogenic composition is contained in unit-dose form. In other embodiments, the immunogenic composition is contained in multi-dose form.

Further provided is a method of enhancing a virus-specific cell-mediated immune response in a subject. In some embodiments, the method includes administering to the subject a silicified virus or silicified virus particles, wherein the virus-specific cell-mediated immune response is increased relative to the cell-mediated immune response following administration of non-silicified virus or non-silicified virus particles.

In some embodiments of the method, the virus infects eukaryotic cells, for example animal cells. In particular embodiments, the virus is a mammalian virus. In some embodiments, the virus is vaccinia virus, a rotavirus, an adenovirus, an influenza virus, a lentivirus, a flavivirus, a hepatitis virus, a parvovirus or a picornavirus. In some examples, the lentivirus is an immunodeficiency virus, such as a human immunodeficiency virus, a simian immunodeficiency virus or a feline immunodeficiency virus. In some examples, the flavivirus is West Nile virus, Japanese encephalitis virus, dengue virus, tick-borne encephalitis virus, yellow fever virus, or St. Louis encephalitis virus. In some examples, the hepatitis virus is hepatitis A virus, hepatitis B virus or hepatitis C virus. In some examples, the picornavirus is poliovirus, hepatitis A virus, rhinovirus or foot and mouth disease virus. In some examples, the parvovirus is an AAV, murine minute virus or a canine parvovirus. In other examples, the virus is respiratory syncytial virus.

In some embodiments, the virus-specific cell-mediated immune response is increased at least 5%, at least 10%, at least 15%, at least 20%, at least 25%, at least 30%, at least 35%, at least 40%, at least 45%, or at least 50%, at least 60%, at least 70%, at least 80%, at least 90% or at least 100% relative to the cell-mediated immune response following administration of non-silicified virus.

In some embodiments, an increase in the virus-specific cell-mediated immune response is determined by an increase in the number of virus-specific T cells, an increase in activation of virus-specific T cells, an increase in cytokine production, or any combination thereof. Accordingly, in some examples, the number of virus-specific T cells following administration of silicified virus or silicified virus particles is increased at least 5%, at least 10%, at least 15%, at least 20%, at least 25%, at least 30%, at least 35%, at least 40%, at least 45%, at least 50%, at least 60%, at least 70%, at least 80%, at least 90% or at least 100%, relative to the number of virus-specific T cells following administration of non-silicified virus or non-silicified virus particles; the activation of virus-specific T cells following administration of silicified virus or silicified virus particles is increased at least 5%, at least 10%, at least 15%, at least 20%, at least 25%, at least 30%, at least 35%, at least 40%, at least 45%, at least 50%, at least 60%, at least 70%, at least 80%, at least 90% or at least 100%, relative to the activation of virus-specific T cells following administration of non-silicified virus or non-silicified virus particles; and/or cytokine production following administration of silicified virus is increased at least 5%, at least 10%, at least 15%, at least 20%, at least 25%, at least 30%, at least 35%, at least 40%, at least 45%, at least 50%, at least 60%, at least 70%, at least 80%, at least 90% or at least 100%, relative to cytokine production following administration of non-silicified virus or non-silicified virus particles.

In some embodiments, the T cells are $CD8^+$ T cells. In other embodiments, the T cells are $CD4^+$ T cells.

In some embodiments, the cytokine is an interleukin (IL), such as IL-1, IL-2, IL-3, IL-4, IL-5, IL-6, IL-7, IL-8, IL-9, IL-10, IL-11, IL-12, IL-13, IL-14, IL-15; IL-16; IL-17; IL-18, IL-19 or IL-20. In some embodiments, the cytokine is an interferon, such as IFN-$\alpha$, IFN-$\beta$, IFN-$\gamma$. In some embodiments, the cytokine is a transforming growth factor (TGF) protein, such as TGF-$\beta$1, TGF-$\beta$2 or TGF-$\beta$3. In some embodiments, the cytokine is a tumor necrosis factor (TNF) family member, such as TNF-$\alpha$, TNF-$\beta$, LT-$\beta$, CD154 or TRAIL. In some embodiments, the cytokine is any other molecule involved in immune regulation, such as erythropoietin, stem cell factor or M-CSF. In one non-limiting example, the cytokine is IFN-$\gamma$.

V. Silicification of Virus or Virus Particles

Methods for silicification of viruses have been described in the art (see, for example, Laidler and Stedman, *Astrobiology* 10:569, 2010; Orange et al., *Biogeosciences* 8:1465, 2011; and Laidler et al., *J Virol* 87(24):13927-13929, 2013).

In addition, exemplary methods for silicification of virus or virus particles are described herein in Example 1 and Example 3.

Generally, silicification is carried out by mixing a selected virus stock with a silica solution, such as a silica solution prepared from sodium metasilicate pentahydrate. The concentration of the silica solution may vary, such as between about 100 ppm and 1000 ppm. In particular methods, the silica solution is about 300 ppm to about 600 ppm (about 5 mM to about 10 mM) silica. Silica solutions may also contain a buffer, such as buffer that increases virus stability. Silica solutions may also contain salts, such as salts that increase virus stability, such as magnesium chloride, calcium chloride, and magnesium sulfate.

In exemplary methods, a small volume (such as about 1-5 mL, or about 2-2.5 mL) of virus in silica solution is injected into dialysis tubing, which is then placed in a larger volume (such as about 30-50 mL, for example 40 mL) of the same concentration of silica solution. The silica solution can be changed periodically, such as about once a day. The duration of incubation of the virus in the silica solution may vary, but is generally about 1 to about 10 days. In some examples, a commercially available dialysis device is used, such as a SLIDE-A-LYZER™ MINI Dialysis Device (Thermo-Fisher).

The present disclosure contemplates the silicification of any virus or virus particle, including any wild-type (i.e. naturally occurring) viruses or particles thereof, or any engineered, recombinant or chimeric viruses or particles thereof. Generally, virus particles are comprised of at least one viral capsid protein and may also include a lipid envelope. Viral particles may or may not include the wild-type or engineered viral genome. For example, virus-like particles, which resemble a virus but do not contain a viral genome, can be silicified according to the methods disclosed herein.

Thus, in the context of the present disclosure, a "virus" includes any family, genus, species, strain or subtype of virus. The term "virus" also includes wild-type, recombinant, chimeric and engineered viruses, and particles thereof. In some embodiments, the virus infects eukaryotic cells, such as animal cells. In particular embodiments, the virus is a mammalian virus (infects mammalian cells). In some embodiments, the virus is a pathogenic virus (i.e. causes disease to the host). In some embodiments, the virus is an enveloped virus. In other embodiments, the virus is a non-enveloped virus.

Examples of viruses (or particles thereof) that can be silicified include, but are not limited to those in the following virus families: Retroviridae (for example, human immunodeficiency virus 1 (HIV-1), HIV-2, human T-cell leukemia viruses; Picornaviridae (for example, poliovirus, hepatitis A virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses, including chikungunya virus, equine encephalitis viruses, Simliki Forest virus, Sindbis virus, Ross River virus, rubella viruses); Flaviridae (for example, hepatitis C virus, dengue virus, yellow fever virus, West Nile virus, St. Louis encephalitis virus, Japanese encephalitis virus, Powassan virus and other encephalitis viruses); Coronaviridae (for example, coronaviruses, severe acute respiratory syndrome (SARS) virus and Middle East respiratory syndrome (MERS) coronavirus); Rhabdoviridae (for example, vesicular stomatitis virus, rabies virus); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses, e.g., murine minute virus, canine parvovirus, the human parvovirus B19, and AAV); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Ban virus; varicella zoster virus; and other herpes viruses, including HSV-6); Poxviridae (variola viruses, vaccinia viruses, pox viruses); and Iridoviridae (such as African swine fever virus); Astroviridae; and unclassified viruses (for example, the agent of delta hepatitis, thought to be a defective satellite of hepatitis B virus).

VI. Immunogenic Compositions and Administration Thereof

The immunogenic compositions provided herein include a silicified virus (or particles thereof), such as a silicified virus capable of infecting mammalian cells. In some cases, the immunogenic compositions further include a pharmaceutically acceptable carrier, an adjuvant, or both. Immunogenic compositions disclosed herein can be used as vaccines to elicit an immune response, such as a protective or therapeutic immune response, against the virus.

The provided immunogenic compositions are typically combined with a pharmaceutically acceptable carrier or vehicle for administration as an immune stimulatory composition to human or animal subjects.

The immunogenic formulations may be conveniently presented in unit dosage form and prepared using conventional pharmaceutical techniques. Such techniques include the step of bringing into association the active ingredient (i.e. the silicified virus or silicified virus particles) and the pharmaceutical carrier(s) or excipient(s). In general, the formulations are prepared by uniformly and intimately bringing into association the active ingredient with liquid carriers. Suitable formulations may include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The immunogenic compositions provided herein may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on, for example, the route of administration and the type of virus. By way of example, intramuscular injections may range from about 0.1 mL to about 1.0 mL. Those of ordinary skill in the art will know appropriate volumes for different routes of administration.

The amount of silicified virus or silicified virus particles in each dose of an immunogenic composition is selected as an amount that induces an immunostimulatory or immunoprotective response without significant, adverse side effects. Such amount will vary depending upon which specific immunogen is employed and how it is presented. Initial injections may range from about 1 μg to about 1 mg, with some embodiments having a range of about 10 μg to about 800 μg, and still other embodiments a range of from about 25 μg to about 500 μg. Following an initial administration of the immunogenic composition, subjects may receive one or several booster administrations, adequately spaced. Booster administrations may range from about 1 μg to about 1 mg, with other embodiments having a range of about 10 μg to about 750 μg, and still others a range of about 50 μg to about 500 μg. Periodic boosters at intervals of 1-5 years, for instance three years, may be desirable to maintain the desired levels of protective immunity.

Administration can be accomplished by single or multiple doses. The dose administered to a subject in the context of the present disclosure should be sufficient to induce a beneficial therapeutic response in a subject over time, or to inhibit or prevent virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

The pharmaceutical or immunogenic compositions or methods of treatment may be administered in combination with other therapeutic treatments. For example, the compositions provided herein can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

The following examples are provided to illustrate certain particular features and/or embodiments. These examples should not be construed to limit the disclosure to the particular features or embodiments described.

EXAMPLES

Example 1

Deactivation, Reactivation and Desiccation Tolerance of Silicified Viruses

This example describes the finding that a diverse group of viruses can be reversibly deactivated by silicification, and in some instances, silicification increases the virus tolerance to desiccation. In the studies described below, the effects of silicification on virus infectivity and resistance to desiccation were determined for four exemplary viruses: two bacteriophages (T4 and PRD1), one enveloped animal virus (vaccinia) and one virus of hyperthermophilic Archaea (SSV-K) (Wiedenheft et al., *J Virol* 78:1954, 2004).

Introduction

One of the major disagreements in virus ecology is whether virus species are cosmopolitan (Breitbart and Rohwer, *Trends Microbiol* 13:278, 2005) or display regional endemism. Studies on viruses in environments as diverse as volcanic hot springs, arctic ice pools and open ocean have generated conflicting results (Angly et al., *PLOS Biology* 4:2121, 2006). Some studies show sharp regional differences between virus genomes (Held and Whitaker, *Environ Microbiol* 11:457, 2009), suggesting limited dispersal. However, several others have found global distribution of viruses with nearly identical genomes in many different environments (Breitbart et al., *FEMS Microbiol Lett* 236:249, 2004; Short and Suttle, *Appl Environ Microbiol* 71:480, 2005).

One study indicates that local virus dispersal can result from aerosolization of the virus by hot spring fumaroles (Snyder et al., *Proc Natl Acad Sci USA* 104:19102, 2007), indicating at least one possible host-independent dispersal mechanism. This result suggests that more distant spread is possible if the virus particles can reach the winds of the stratosphere and upper troposphere (Smith et al., *Aerobiologia* 26:35, 2010). Several studies have shown that these upper level winds are capable of carrying bacteria and fungi from the Sahara Desert as far as the glaciers of Mont Blanc (Chuvochina et al., *Microbiology* 80:125, 2011; Chuvochina et al., *Microbes Environ* 26:237, 2011; Hervas et al., *Environ Microbiol* 11:1612, 2009; Laghdass et al., *Aquat Microb Ecol* 62:201, 2011; Perfumo and Marchant, *Environ Microbiol Rep* 2:333, 2010; Prospero et al., *Aerobiologia* 21:1, 2005; Schlesinger et al., *Aerobiologia* 22:259, 2006; Toepfer et al., *Aerobiologia* 28:221, 2012).

A critically limiting factor for wind-borne virus spread is the ability of the virus to resist drying; most viruses are very sensitive to desiccation (Ding et al., *Gynecol Oncol* 121:148, 2011; Fogarty et al., *Virus Res* 132:140, 2008; Nakano et al., *Fish Pathol* 33:65, 1998) and rapidly lose infectivity when aerosolized. However, if viruses could be reversibly coated in a protective layer in addition to their capsid, they could potentially spread very widely. Silica coating is a particularly attractive possibility, since prior studies have shown that viruses can be coated with silica under simulated natural hot spring conditions (Laidler and Stedman, *Astrobiology* 10:569, 2010; Orange et al., *Biogeosciences* 8:1465, 2011).

Methods

Bacteriophage T4, PRD1 and SSV-K virus stocks originated from laboratory stocks. All stocks were made fresh from either frozen stock (SSV-K) or maintained in their native host (T4 and PRD1). For each of these viruses, 100 mL of log-phase host culture (*Escherichia coli* B for T4, *Salmonella typhimurium* LT2 for PRD1 and *Sulfolobus solfataricus* GΘ for SSV-K) was inoculated with a 1 mL aliquot of the laboratory virus stock and incubated at an appropriate temperature (37° C. for *E. coli* and *S. typhimurium*; 80° C. for *S. solfataricus* GΘ). After overnight incubation, the infected cultures were centrifuged at 3000 g for 30 minutes to pellet cells and cellular debris. The SSV-K culture was adjusted to a pH of 7.0 with 1M $NaHCO_3$ prior to centrifugation because SSV virus particles are more stable at neutral pH than they are at the optimal pH of their host (pH 2-3). After centrifugation, the supernatant was decanted and filtered through a 0.2 μm surfactant-free cellulose acetate filter into a sterile polypropylene container. Virus stocks were prepared the day before the start of the experiments and stored at 4° C. until used.

At the start of the experiment, the virus stocks were mixed with silica solutions freshly prepared from sodium metasilicate pentahydrate to yield final concentrations of 0, 300 and 600 ppm (0, 5 and 10 mM, respectively) silica. The solutions also contained 10 mM $NaHCO_3$ (buffer) and 5 mM $MgCl_2$ (increases virus stability) and were adjusted to a pH of 7.0-7.1 with 1N HCl. Initial trials using silica concentrations of 150 ppm and 200 ppm showed no detectable difference between those solutions and the 0 ppm control solution with respect to virus infectivity.

The final virus titers were approximately $10^9$ pfu/mL for T4, PRD1 and VACV and $10^5$ pfu/mL for SSV-K. Between 2.0 and 2.5 mL of each solution were then injected into individual sections of dialysis tubing (10 mm, 12,000 Dalton MWCO) that were sealed at one end by an injection septum. This dialysis tubing was then immersed in 40 mL of bathing solution with the same silica, $NaHCO_3$, $MgCl_2$ and pH as the virus solution.

The bathing solution was replaced each day with freshly prepared solution of the same composition and samples were withdrawn through the injection septum on days 0 (within ten minutes of the start of the experiment), 1, 3, 8 and 10. The virus titer of each sample was determined in triplicate by plaque assay.

On day 10, 100 μL aliquots were taken in triplicate for desiccation tests. Also on day 10, 100 μL sample aliquots were taken and diluted to 1 mL with 0 ppm silica solution, reducing the silica concentration below saturation. Plaque assays were performed on these diluted samples on days 12, 14, 16 and 20 to determine if any loss of infectivity was reversible.

The desiccation sample aliquots were placed in polypropylene microcentrifuge tubes and initial drying was done in a vacuum concentrator at 4° C. and 13 mBar for 4 hours before placing the samples in a vacuum desiccator with fresh desiccant at a pressure of 240-270 mBar until time for analysis, which was performed after 10, 30 and 90 days of desiccation. At the time of analysis, the desiccated virus sample was rehydrated with 1 mL of 0 ppm silica solution. One hour after rehydration and ten days after rehydration, 100 μL samples were taken and the virus titer determined by plaque assay. For the SSV-K samples, the entire 1 mL of rehydrated virus solution was used in the 10 day and 30 day analyses to increase the sensitivity of the plaque assay.

Vaccinia virus (VACV) required a slightly different experimental procedure. Virus stocks were prepared ahead of time by infecting planktonic HeLa cells and incubating the culture at 37° C. for 48 hours. The entire culture solution was then frozen and stored at –80° C. until needed. At the start of each experiment, an aliquot of VACV was thawed at 37° C., vortexed vigorously and then mixed with freshly prepared sodium metasilicate solution to a final concentration of either 0 ppm or 600 ppm.

For VACV silicification, desilification and desiccation studies, the base solution was Dulbecco's phosphate buffered saline (DPBS), pH adjusted to 7.0-7.1 with 1 N HCl. DPBS was chosen because of studies showing that VACV is stable in DPBS at room temperature (Kline et al., *Vaccine* 23:4944, 2005; Newman et al., *J Infect Dis* 187:1319, 2003). In addition, the exposure to silica solution was carried out in polypropylene microcentrifuge tubes instead of dialysis tubing and the exposure lasted only two days, without refreshing the solution. After two days, a 100 μL aliquot was removed and diluted with 900 μL of DPBS, yielding a final silica concentration of 60 ppm (1 mM), which is below the saturation concentration of silica at room temperature (Conrad et al., *Geochim Cosmochim Acta* 71:531, 2007; Gunnarsson and Arnorsson, *Geothermics* 34:320, 2005). Finally, the desiccation experiments were performed at ambient atmospheric pressure in a BSL3 laminar flow hood to avoid the risk of contaminating equipment with VACV.

Results

It was not previously known whether silica coating affects virus infectivity. Thus, the effect of silicification on the infectivity of four diverse viruses was determined. The viruses used in this study included two bacteriophages (T4 and PRD1) (Bamford et al., *Adv Virus Res* 45:281, 1995; J. D. Karam, Ed., *Bacteriophage T4*, ASM Press, Washington, D.C., ed. 2nd, 1994); one enveloped animal virus (Vaccinia) (Smith et al., *J Gen Virol* 83:2915, 2002); and one virus of hyperthermophilic Archaea (SSV-K) (Wiedenheft et al., *J Virol* 78:1954, 2004). The viruses were incubated in solutions with initial dissolved silica concentrations that ranged from 0 ppm (control) to 600 ppm at pH 7.0-7.1 for ten days. Results of replicate experiments with 150 ppm and 200 ppm silica concentrations were indistinguishable from those with 0 ppm. During the initial incubation, samples were taken periodically and virus infectivity determined by plaque assays. Treatment of bacteriophage PRD1 with silica at any of the experimental concentrations has practically no effect on infectivity. By contrast, treatment of bacteriophage T4 with either 300 ppm (5 mM) or 600 ppm (10 mM) silica has a dramatic effect on infectivity, with nearly three orders of magnitude loss of infectivity on exposure to 600 ppm silica at ten days (FIG. 1A). Exposure to 600 ppm silica solution had a greater impact than exposure to 300 ppm silica solution. This finding was surprising, given the previous finding that bacteriophage T4 exposed to 300 ppm silica solution are uniformly coated in amorphous silica (Laidler and Stedman, *Astrobiology* 10:569, 2010). Interestingly, the archaeal fusellovirus SSV-K, which is endogenous to high-silica hot spring environments, has an intermediate degree of inactivation (FIG. 1A). Bacteriophage T4, PRD1 and the archaeal virus SSV-K have protein coats (Bamford et al., *Adv Virus Res* 45:281, 1995; J. D. Karam, Ed., *Bacteriophage T4*, ASM Press, Washington, D.C., ed. 2nd, 1994; Wiedenheft et al., *J Virol* 78:1954, 2004).

The other major virus morphology, and that of many pathogenic animal viruses, is enveloped or having an exterior lipid membrane. Therefore, the response of the well-characterized enveloped animal virus, vaccinia virus (VACV) to silica treatment was tested. After only two days of exposure to 600 ppm silica solution, the infectivity of VACV was reduced more than three orders of magnitude (FIG. 1A), while the most susceptible of the three non-enveloped viruses—bacteriophage T4—lost less than two orders of magnitude of infectivity in that time (FIG. 1A). For technical reasons, the assay conditions for VACV were somewhat different than for bacteriophage T4, so the two may not be directly comparable. The silica concentrations needed to affect infectivity are significantly higher than the concentrations needed for homogenous nucleation.

Based on previous silicification studies with bacteria and archaea (Laidler and Stedman, *Astrobiology* 10:569, 2010; Orange et al., *Biogeosciences* 8:1465, 2011; Asada and Tazaki, *Can Mineral* 39:1, 2001; Benning et al., *Geochim Cosmochim Acta* 68:743, 2004; Kyle et al., *Geomicrobiol J* 24:627, 2007; Orange et al., *Geobiology* 7:403, 2009; Peng et al., *Chin Sci Bull* 52:367, 2007; Phoenix et al., *Chem Geol* 169:329, 2000; Renaut et al., *Sedimentology* 45:1083, 1998; SchultzeLam et al., *Can J Earth Sci* 32:2021, 1995; Toporski et al., *Astrobiology* 2:1, 2002; Westall et al., *Palaeontology* 38:495, 1995), loss of virus infectivity on silicification is not surprising. More surprising is that, even in supersaturated silica solutions, different viruses were not equally affected. Bacteriophage T4 is nearly completely inactivated, PRD1 has no detectable loss of infectivity and SSV-K has an intermediate response. Although the experimental methods used for VACV were different, the data suggest that VACV may be even more susceptible to silicification than bacteriophage T4, probably due to its lipid membrane coat. These findings strongly suggest that the surface characteristics of different viruses significantly impact the rate of silica deposition and thereby their susceptibility to inactivation by silicification.

In order to determine if loss of infectivity with silicification was reversible, an aliquot of each of the viruses after ten days' exposure to 600 ppm silica solution was placed into a 0 ppm silica solution. Aliquots of viruses that had not been silicified were used as controls. Samples were removed for up to 10 additional days and virus infectivity was determined. Both bacteriophage T4 and SSV-K regained infectivity to at least 10% of their initial titer within ten days of exposure to the low silica solution (FIG. 1A). Similarly, silicified VACV recovered about 90% of its infectivity when placed in a solution undersaturated with silica (FIG. 1A). Beyond showing that the effect of silicification on infectivity is reversible under these conditions, these results support the hypothesis that the effect on infectivity was due to coating with silica rather than physical or chemical damage, which would have been irreversible.

Finally, the results show that silicified bacteriophage T4 and the archaeal virus SSV-K have enhanced resistance to desiccation compared to the unsilicified virus. After ten days of silicification, an aliquot of each virus-silica combination was placed in a vacuum desiccator. Desiccated samples were analyzed after 10, 30 and 90 days. Treated viruses were diluted 1:10 in 0 ppm silica to discern whether loss of infectivity was reversible. Untreated virus served as a control. Virus infectivity was determined immediately after desiccation. Silicified bacteriophage T4 was stable to at least 30 days of desiccation, whereas unsilicified virus was irreversibly inactivated. SSV-K was similarly protected by silicification (FIG. 1B), but to a lesser extent than bacteriophage T4. Because SSV-K cannot be grown to the high titers of bacteriophage T4, the detection limit of this virus is lower, limiting the ability to compare their desiccation resistance at longer exposures. However, protection was not absolute, as there was more than a seven order of magnitude loss of infectivity of bacteriophage T4 after 90 days of desiccation, to below the limits of detection for the assay.

Among the unsilicified viruses, only VACV had any infectivity after desiccation. The desiccation resistance of VACV was reduced after two days of silicification. The infectivity of unsilicified VACV dropped three orders of magnitude after desiccation ($1.4 \times 10^8$ pfu/mL to $2.1 \times 10^5$ pfu/mL) while the silicified VACV dropped four orders of magnitude ($1.4 \times 10^8$ pfu/mL to $1.6 \times 10^4$ pfu/mL). This loss of infectivity of VACV is consistent with the innate desiccation resistance of the virus under the experimental conditions (Collier, *Bacteriol Rev* 18:74, 1954).

These desiccation results indicate that, for at least some viruses, silicification may protect them from the effects of drying. This may allow for virus persistence for at least several weeks under stratospheric pressures and humidity. If hot spring viruses were silicified and aerosolized by outgassing or fumarole activity, the silicification could allow viruses to persist for days to weeks under stratospheric pressure and humidity and might allow global dispersal (Smith et al., *Aerobiologia* 26:35, 2010), potentially explaining some of the conflicting results discussed above (Breitbart et al., *FEMS Microbiol Lett* 236:249, 2004; Short and Suttle, *Appl Environ Microbiol* 71:480, 2005; Breitbart and Rohwer, *Trends Microbiol* 13:278, 2005; Angly et al., *PLOS Biology* 4:2121, 2006; Held and Whitaker, *Environ Microbiol* 11:457, 2009).

Above and beyond the implications for virus dispersal, virus silicification can serve as a method for vaccine preservation. Vaccines against infectious disease are the most cost-effective ways of treating disease (Anonymous, *Bulletin of the World Health Organization* 78:274, 2000; Jefferson, *Vaccine* 17:S69, 1999). However, some vaccines are highly labile, which compromises delivery, particularly in the developing world (Levine and Robins-Browne, *Immunol Cell Biol* 87:274, 2009). Silica coating these vaccines allows them to be delivered and processed for much lower cost than previously possible.

Example 2

Immune Response Following Administration of Silicified and Non-silicified VACV

This example describes the finding that silicified virus is capable of inducing a virus-specific immune response following administration in vivo.

To determine whether silicified virus is capable of infecting and inducing an immune response in an animal host, C57BL/6 mice were administered prime and booster inoculations of $1 \times 10^6$ pfu of either silicified or non-silicified VV-OVA (recombinant vaccinia virus expressing ovalbumin). Antigen-specific T cells were measured by intracellular cytokine staining (ICS) and MHC tetramer staining seven days following the prime inoculation and five days following the booster inoculation (FIG. 2).

Figure 3:
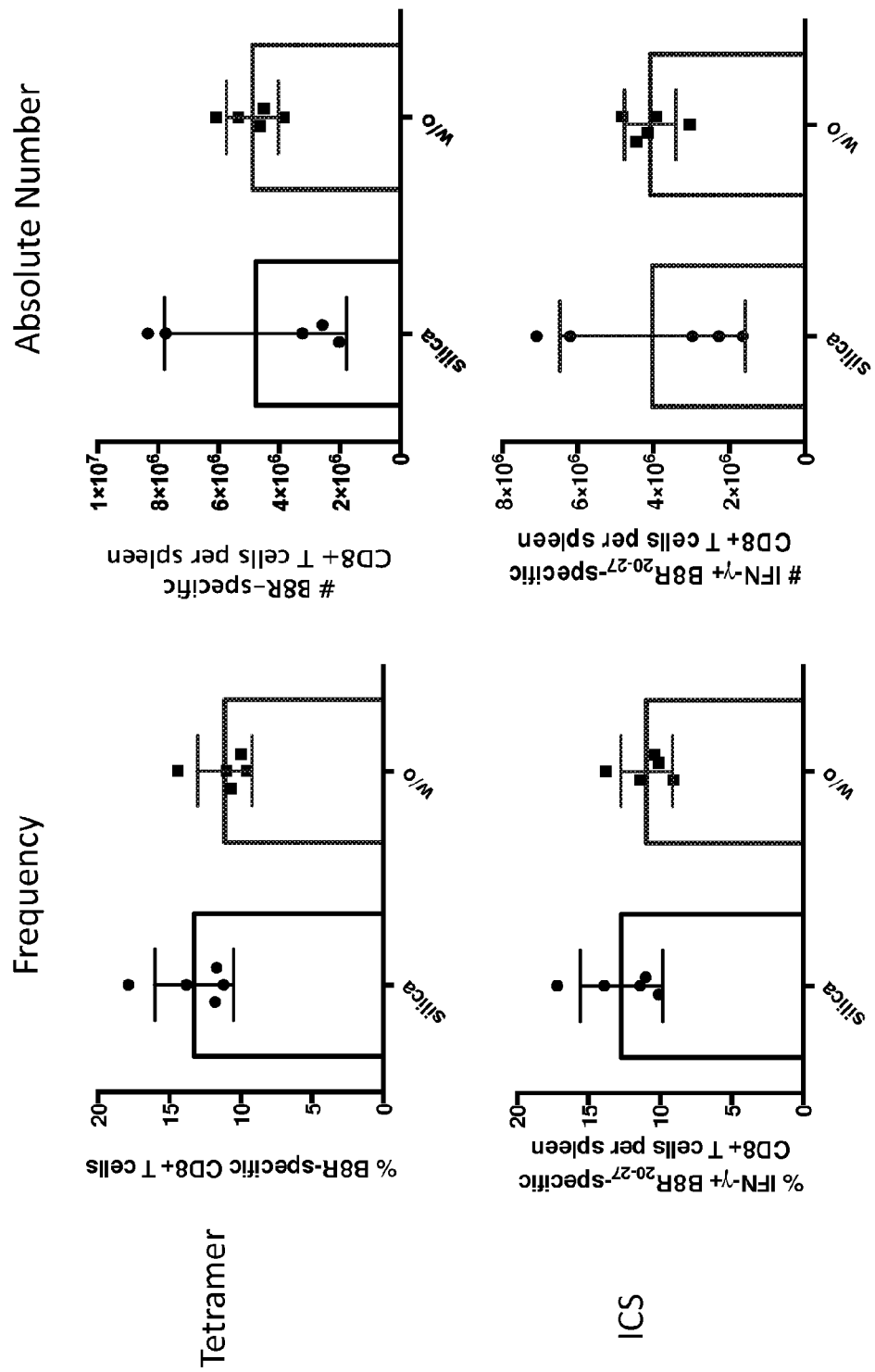
FIG. 3 is a series of graphs showing the frequency and number of VACV B8R antigen-specific CD8$^+$ T cells, and IFN-γ+/B8R-specific T cells following administration of silicified and non-silicified VACV.
Figure 5:
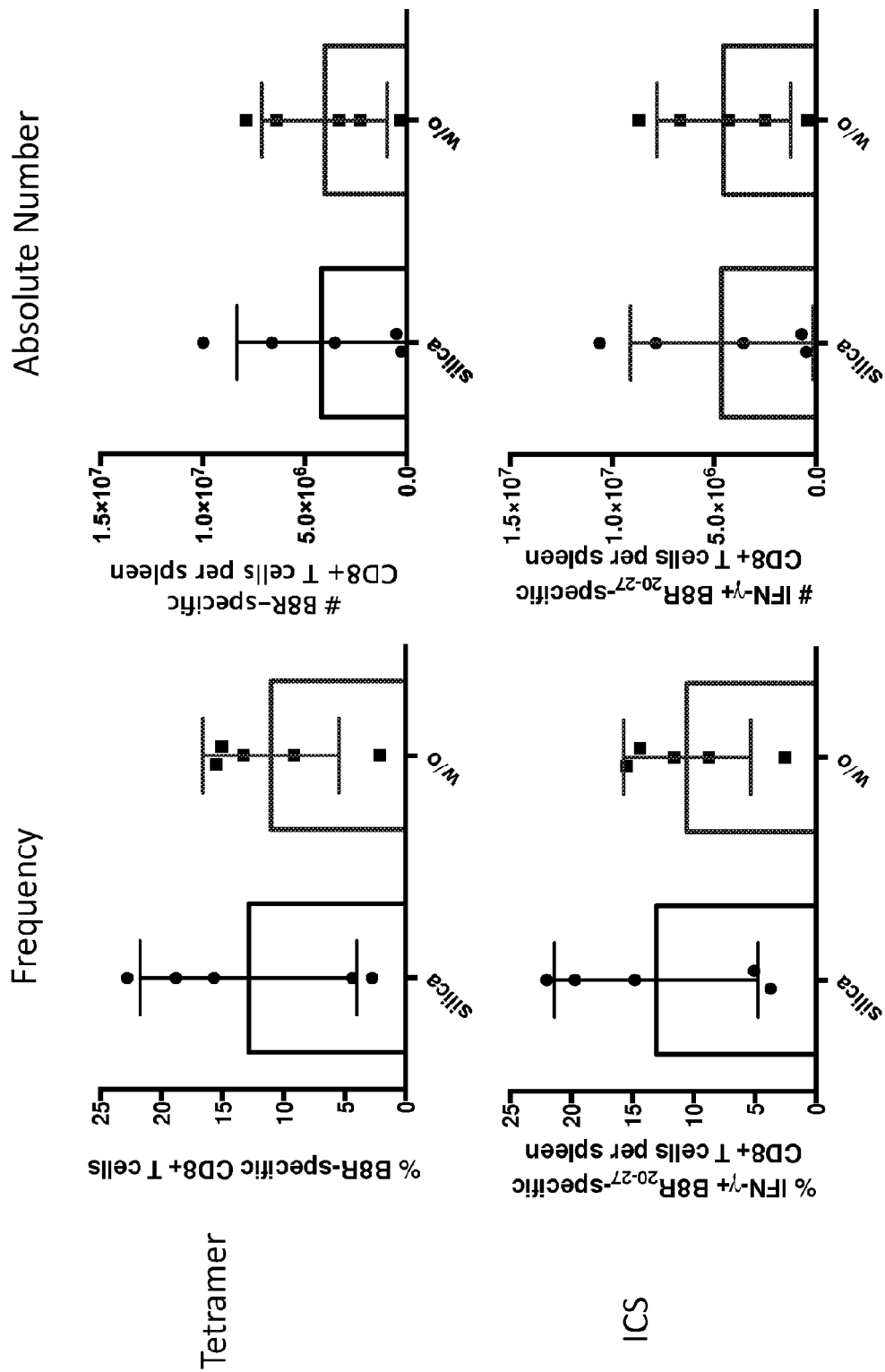
FIG. 5 is a series of graphs showing the frequency and number of VACV B8R antigen-specific $CD8^+$ T cells, and IFN-γ+/B8R-specific T cells following booster administration of silicified and non-silicified VACV.

Tetramer staining and ICS were performed to evaluate the frequency and number of virus antigen-specific T cells obtained from the spleen of inoculated animals. MHC tetramers specific for the VACV B8R peptide epitope were used to quantify antigen-specific CD8$^+$ T cells. ICS was carried out to measure IFN-γ+/B8R-specific T cells. As shown in FIG. 3 (prime) and FIG. 5 (boost), silicified and non-silicified VACV induced similar numbers of virus-specific CD8$^+$ T cells and IFN-γ expressing virus-specific CD8$^+$ T cells.

Figure 4:
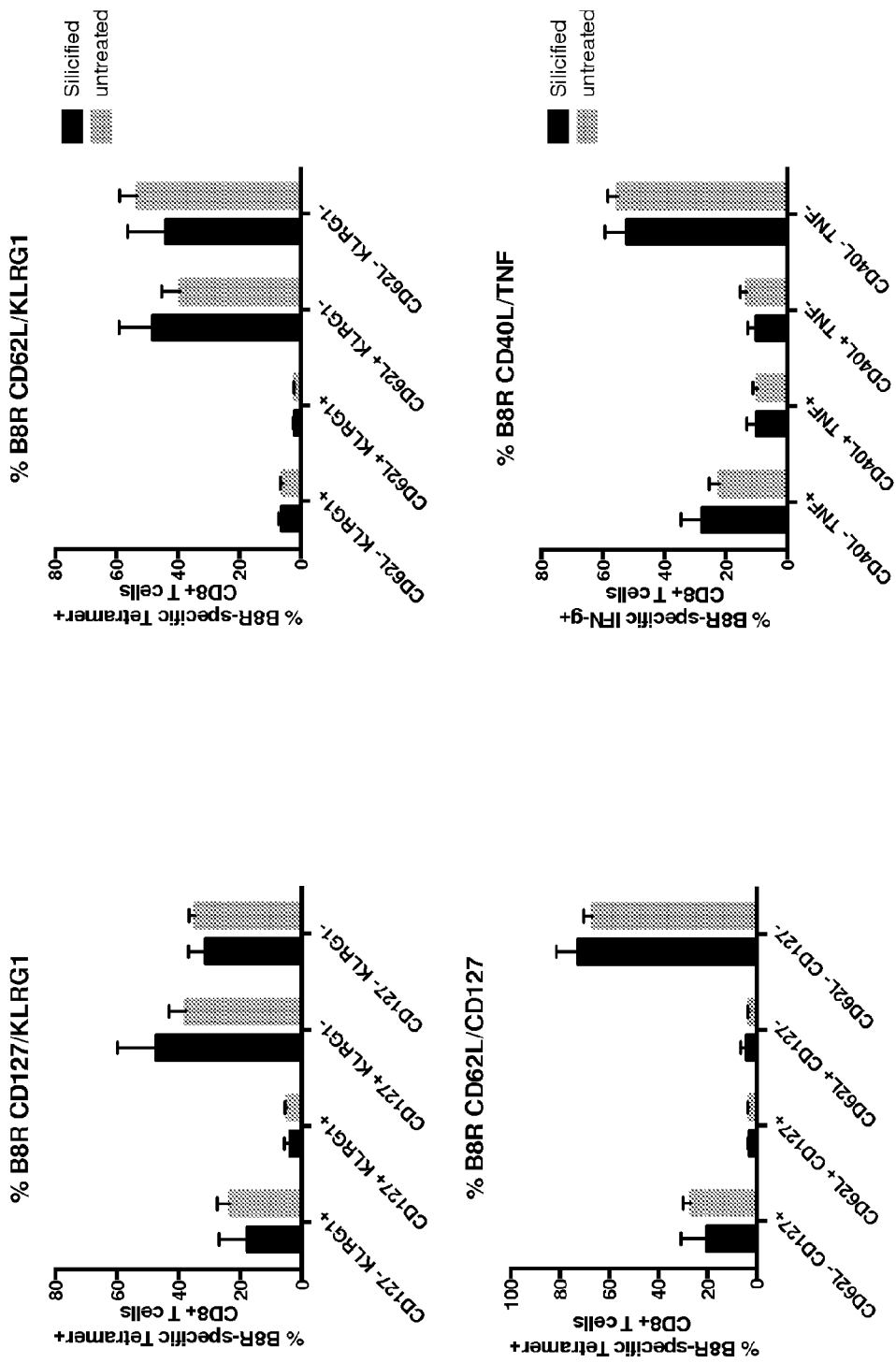
FIG. 4 is a series of graphs showing the percentage of VACV B8R antigen-specific effector and memory T cells following administration of silicified and non-silicified VACV.

Additional studies were carried out to evaluate memory and effector T cell subsets in mice inoculated with silicified and non-silicified VV-OVA. As shown in FIG. 4 (prime) and FIG. 6 (boost), no significant difference was observed in the percentage of virus-specific effector and memory T cells following administration of silicified and non-silicified VV-OVA.

These data demonstrate that silicified VACV can shed its silica coat and be infectious in mice. These results further demonstrate that silicified virus is capable of inducing a virus-specific immune response in vaccinated animals.

Example 3

Silicification of Bacteriophage PhiX174 as a Model for Small Viruses

This example describes the finding that silicification can significantly reduce infectivity of very small viruses.

In this study, two similar silicification procedures were compared—silicification using a SLIDE-A-LYZER™ MINI Dialysis Device (10K MWCO, 0.5 mL units; Thermo-Fisher Catalog number 88401), and the standard silicification procedure described in Example 1. These procedures are identical other than the device used for dialysis. Very similar results were obtained with both protocols.

Bacteriophage PhiX174 is a very small (about 30 nm diameter) non-enveloped virus that serves as a model for picornaviruses, such as poliovirus, hepatitis A virus, rhinoviruses, and foot and mouth disease virus, as well as parvoviruses, such as adeno-associated virus (AAV), minute virus of mice, and canine parvoviruses.

Plaque forming units (PFU) were determined using *E. coli* C as a host on diluted PhiX174 virus preparations that had been unexposed to SiO$_2$ (No SiO$_2$) or exposed to silicifying conditions for 4 days (Table 1) or seven days (Table 2). Two different silicification protocols were used, one using a commercial SLIDE-A-LYZER unit and the other using the silicification protocol described in Example 1 and in Laidler et al. (*J Virol* 87(24):13927-13929, 2013). In each table, "A" and "B" are replicate assays.

TABLE 1

PFU following exposure of PhiX174 to silicification conditions for four days

| | Replicate | |
|---|---|---|
| | A | B |
| Dilution | 10$^{-7}$ | 10$^{-7}$ |
| Plus SiO$_2$ SLIDE-A-LYZER ™ | 14 | 37 |
| Plus SiO$_2$ standard silicification | 7 | 13 |
| No SiO$_2$ | 107 | 103 |

TABLE 2

PFU following exposure of PhiX174 to silicification conditions for seven days

| | Replicate | | | |
|---|---|---|---|---|
| | A | B | A | B |
| Dilution | 10$^{-7}$ | 10$^{-7}$ | 10$^{-6}$ | 10$^{-6}$ |
| Plus SiO$_2$ SLIDE-A-LYZER ™ | 1 | 0 | 4 | 19 |
| No SiO$_2$ | ca.100 | n.d. | n.d. | n.d. |

"n.d." = not determined

As shown in Tables 1 and 2, use of either silicification procedure resulted in a significant decrease in viral infectivity, compared to dialysis in the absence of SiO$_2$. These results indicate that silicification is possible for even very small viruses, including human viruses, such as AAV, poliovirus and hepatitis A virus.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of inducing a virus-specific immune response in a subject, comprising administering to the subject an effective amount of silicified virus or silicified virus particles, thereby inducing a virus-specific immune response in the subject.

2. The method of claim 1, wherein the virus is vaccinia virus, a rotavirus, an adenovirus, an influenza virus, a lentivirus, a flavivirus, a hepatitis virus, a picornavirus, or a coronavirus.

3. The method of claim 2, wherein the virus is a lentivirus and the lentivirus is an immunodeficiency virus.

4. The method of claim 3, wherein the immunodeficiency virus is a human immunodeficiency virus.

5. The method of claim 2, wherein the virus is a flavivirus and the flavivirus is West Nile virus, Japanese encephalitis virus, dengue virus, tick-borne encephalitis virus, yellow fever virus, or St. Louis encephalitis virus.

6. The method of claim 2, wherein the virus is a hepatitis virus and the hepatitis virus is hepatitis A virus, hepatitis B virus or hepatitis C virus.

7. The method of claim 2, wherein virus is a picornavirus and the picornavirus is poliovirus.

8. The method of claim 2, wherein the virus is a coronavirus and the coronavirus is severe acute respiratory syndrome (SARS) virus or Middle East respiratory syndrome (MERS) coronavirus.

9. The method of claim 1, wherein the virus-specific immune response comprises activation of virus-specific T cells, production of virus-specific antibodies, cytokine production, or any combination thereof.

10. The method of claim 1, wherein administration is by a route selected from intramuscular, subcutaneous, oral and inhalation.

11. An immunogenic composition comprising (i) a silicified virus or silicified virus particles and (ii) a pharmaceutically acceptable carrier or an adjuvant, wherein the virus is vaccinia virus, a rotavirus, an adenovirus, an influenza virus, a lentivirus, a flavivirus, a hepatitis virus, a picornavirus or a coronavirus.

12. The immunogenic composition of claim 11, wherein
the virus is a lentivirus and the lentivirus is an immunodeficiency virus;
the virus is a flavivirus and the flavivirus is West Nile virus, Japanese encephalitis virus, dengue virus, tick-borne encephalitis virus, yellow fever virus, or St. Louis encephalitis virus;
the virus is a hepatitis virus and the hepatitis virus is hepatitis A virus, hepatitis B virus or hepatitis C virus;
the virus is a picornavirus and the picornavirus is poliovirus; or
the virus is a coronavirus and the coronavirus is SARS virus or MERS virus.

13. The immunogenic composition of claim 12, wherein the virus is a lentivirus and the lentivirus is a human immunodeficiency virus.

14. The immunogenic composition of claim 11, wherein the adjuvant comprises a water-in-oil emulsion, incomplete Freund's adjuvant, alum, aluminum hydroxide, a toll-like receptor agonist, an immunostimulatory oligonucleotide or a biological adjuvant.

15. The immunogenic composition of claim 11, wherein the pharmaceutically acceptable carrier comprises physiological saline, balanced salt solution, buffering agent, suspending agent, thickening agent, non-aqueous solvent, aqueous carrier, preservative, anti-oxidant, bacateriostat, or any combination thereof.

16. The immunogenic composition of claim 11, contained in unit-dose form.

17. The immunogenic composition of claim 11, wherein the silicified virus is silicified attenuated virus.

18. The immunogenic composition of claim 11, wherein the virus particles are virus-like particles.

19. The method of claim 1, wherein the silicified virus is silicified attenuated virus.

20. The method of claim 1, wherein the virus particles are virus-like particles.

* * * * *